United States Patent [19]

Takamura et al.

[11] Patent Number: 4,853,404
[45] Date of Patent: Aug. 1, 1989

[54] PHENOXYACETIC ACID DERIVATIVES COMPOSITION AND USE

[75] Inventors: Norio Takamura, Asaka; Kuniyuki Oda, Urawa; Shinichi Kodato, Kawaguchi; Isao Yamaguchi, Tokyo; Koji Yano, Hoya, all of Japan

[73] Assignee: Tanabe Seiyaku Co., Ltd., Osaka, Japan

[21] Appl. No.: 105,173

[22] Filed: Oct. 5, 1987

[30] Foreign Application Priority Data

Oct. 13, 1986 [JP] Japan .................. 61-242802

[51] Int. Cl.$^4$ ............. A61K 31/415; C07D 231/12
[52] U.S. Cl. ................... 514/406; 548/376; 548/377; 548/378
[58] Field of Search .......... 548/377, 378, 376; 514/406, 407

[56] References Cited

FOREIGN PATENT DOCUMENTS 4817272 10/1970 Japan .................................... 549/483
1268321 3/1972 United Kingdom ................ 546/314
1415295 11/1975 United Kingdom ................ 546/314
2024209 1/1980 United Kingdom ................ 546/314

*Primary Examiner*—Robert W. Ramsuer
*Attorney, Agent, or Firm*—Browdy & Neimark

[57] ABSTRACT

Novel phenoxyacetic acid derivatives of the formula:

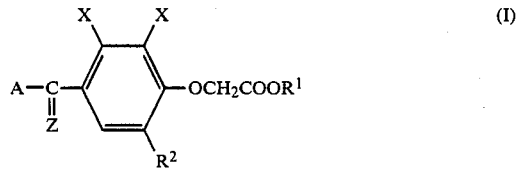

wherein A is a substituted or unsubstituted 5-pyrazolyl group, $R^1$ is hydrogen atom or a lower alkyl group, $R^2$ is hydrogen atom or a lower alkenyl group, X is a halogen atom and Z is oxygen atom or methylene group, and salts thereof have potent diuretic, saluretic and uricosuric activities.

13 Claims, No Drawings

PHENOXYACETIC ACID DERIVATIVES COMPOSITION AND USE

This invention relates to a phenoxyacetic acid derivative and processes for preparing the same. More particularly, it relates to a phenoxyacetic acid derivative of the formula:

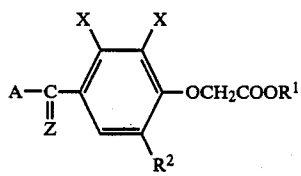

wherein A is a substituted or unsubstituted 5-pyrazolyl group, $R^1$ is hydrogen atom or a lower alkyl group, $R^2$ is hydrogen atom or a lower alkenyl group, X is a halogen atom and Z is oxygen atom or methylene group, or a salt thereof.

Known diuretics agents include thiazide diuretics such as chlorothiazide or hydrochlorothiazide and loop diuretics such as furosemide or ethacrynic acid. These agents are useful to increase urine volume and electrolyte excretion by inhibiting reabsorption of water and electrolytes from renal tubules. However, these known diuretics are not satisfactory in that they are liable to cause hyperuricemia which often results in interstitial nephritis or gout due to deposition of uric acid in tissue of living body. Therefore, it has been wanted to develop diuretics which can promote excretion of not only water and electrolytes but also uric acid.

We have now found that the phenoxyacetic acid derivative (I) and its salts have potent diuretic, saluretic and uricosuric activities. For example, when the effect of a test compound on urine volume was examined by administering a carboxymethylcellulose solution thereof (dose: 100 mg/kg) orally to saline-loaded rats, each one of [2,3-dichloro-4-(1-ethoxymethyl-5-pyrazolylcarbonyl)phenoxy]acetic acid, [2,3-dichloro-4-(1-methoxymethyl-5-pyrazolylcarbonyl)phenoxy]acetic acid, [2,3-dichloro-4-(1-ethyl-5-pyrazolylcarbonyl)phenoxy]acetic acid and [2,3-dichloro-4-(1-isopropyl-5-pyrazolylcarbonyl)phenoxy]acetic acid showed more than 100% increase in the urine volume as compared with a control group of rats. Moreover, the oral administration of [6-allyl-2,3-dichloro-4-(1-methyl-5-pyrazolylcarbonyl)phenoxy]acetic acid or {2,3-dichloro-4-[1-(1-methyl-5-pyrazolyl)vinyl]phenoxy}acetic acid to said saline-loaded rats produced more than 100% increase in the uric acid excretion as compared with a control group of rats.

Examples of the compound of the present invention include those of the formula (I) in which A is 5-pyrazolyl group or a substituted 5-pyrazolyl group; $R^1$ is hydrogen atom or a lower alkyl group such as methyl, ethyl, propyl or butyl; $R^2$ is hydrogen atom or a lower alkenyl group such as vinyl, propenyl or butenyl; X is a halogen atom such as chlorine, bromine or iodine; and Z is oxygen atom or methylene group.

When A is a substituted 5-pyrazolyl group, examples of such substituted 5-pyrazolyl group include a 5-pyrazolyl group having at least one substituent selected from a halogen atom such as chlorine or bromine; an alkyl($C_{1-10}$) group such as methyl, ethyl, propyl, isopropyl, butyl or pentyl; a cycloalkyl($C_{3-8}$) group such as cyclopentyl or cyclohexyl; an aryl group such as phenyl; an aryl-lower alkyl group such as benzyl or phenethyl; a lower alkoxy-lower alkyl group such as methoxymethyl or ethoxymethyl; a lower alkoxy-lower alkoxy-lower alkyl group such as methoxymethoxymethyl or methoxyethoxymethyl; a di(lower alkyl)amino-lower alkyl group such as dimethylaminomethyl or dimethylaminoethyl; a lower alkanoyl group such as acetyl or propionyl; an arylcarbonyl group such as benzoyl; a lower alkoxycarbonyl group such as tert-butoxycarbonyl; and a di- or triphenyl-lower alkyl group such as benzhydryl or trityl.

Among the compounds of the present invention, a preferred subgenus is that of the formula (I) in which A is 5-pyrazolyl group or a 5-pyrazolyl group having at least one substituent selected from a halogen atom, an alkyl($C_{1-10}$) group, a cycloalkyl($C_{3-8}$) group, phenyl group, an phenyl-lower alkyl group, a lower alkoxy-lower alkyl group, a lower alkoxy-lower alkoxy-lower alkyl group and a di(lower alkyl)amino-lower alkyl group; $R^1$ is hydrogen atom or a lower alkyl group; $R^2$ is hydrogen atom or allyl (=2-propenyl); X is chlorine atom; and Z is oxygen atom or methylene group.

Another preferred subgenus is those of the formula (I) in which A is 5-pyrazolyl group, a 1-lower alkyl-5-pyrazolyl group, a 1-lower alkyl-4-halogeno-5-pyrazolyl group, a 1-cycloalkyl($C_{3-8}$)-5-pyrazolyl group, 1-phenyl-5-pyrazolyl group, a 1-(phenyl-lower alkyl)-5-pyrazolyl group, a 1-(lower alkoxy-lower alkyl)-5-pyrazolyl group, a 1-(lower alkoxy-lower alkoxy-lower alkyl)-5-pyrazolyl group or a 1-(di(lower alkyl)amino-lower alkyl)-5-pyrazolyl group; $R^1$ is hydrogen atom or a lower alkyl group; $R^2$ is hydrogen atom or allyl; X is chlorine atom; and Z is oxygen atom or methylene.

Another preferred subgenus is that of the formula (I) in which A is a 1-lower alkyl-5-pyrazolyl group, a 1-lower alkyl-4-halogeno-5-pyrazolyl group or a 1-(lower alkoxy-lower alkyl)-5-pyrazolyl group, $R^1$ is hydrogen atom, $R^2$ is hydrogen atom or allyl, X is chlorine atom, and Z is oxygen atom or methylene.

According to the present invention, the phenoxyacetic acid derivative (I) or a salt thereof can be prepared by the step or steps of:

(A)-(i) reacting a phenol compound of the formula:

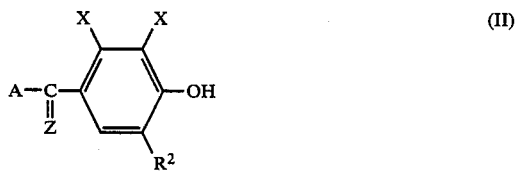

wherein A, $R^2$, X and Z are the same as defined above, with an acetic acid compound of the formula:

wherein Y is a reactive residue and $R^1$ is the same as defined above, to give the compound (I); or (-ii) oxidizing a compound of the formula:

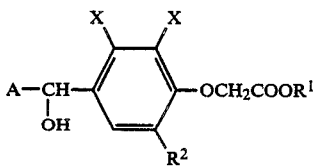

wherein A, $R^1$, $R^2$ and X are the same as defined above, to give a compound of the formula:

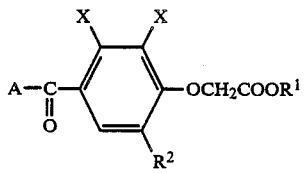

wherein A, $R^1$, $R^2$ and X are the same as defined above; or (-iii) reacting the compound (I-A) with an ylide compound of the formula:

$$(C_6H_5)_3P=CH_2 \qquad (V)$$

to give a compound of the formula:

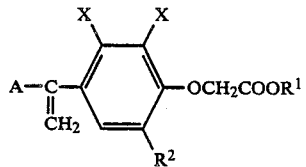

wherein A, $R^1$, $R^2$ and X are the same as defined above; or (-iv) hydrolysing a compound of the formula:

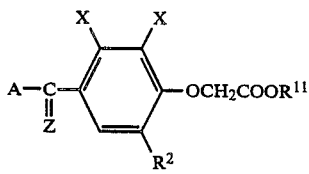

wherein $R^{11}$ is a lower alkyl group and A, $R^2$, X and Z are the same as defined above, to give a compound of the formula:

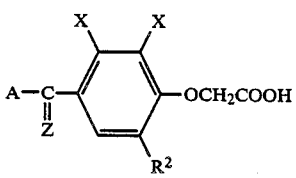

wherein A, $R^2$, X and Z are the same as defined above; and (B) if required, further converting the product into a salt thereof.

(C) When A is a 5-pyrazolyl group having a substituent selected from a lower alkoxy-lower alkyl group, a lower alkanoyl group, an arylcarbonyl group, a lower alkoxycarbonyl group and di- or triphenyl lower alkyl group at the $N^1$-position thereof, said substituent may be, if required, removed from the compound obtained in the Step (A) before the above-mentioned Step (B). Alternatively, (D) when A is a 4-unsubstituted-5-pyrazolyl group, the compound obtained in the Step (A) may be, if required, halogenated before the above-mentioned Step (B) and either before or after Step (C) to give the corresponding 4-halogeno-5-pyrazolyl compound.

Examples of the reactive residue Y in the starting compound (III) include a halogen atom such as chlorine, bromine or iodine, tosyloxy and methanesulfonyloxy.

The reaction of the phenol compound (II) with the acetic acid compound (III) can be carried out in a solvent in the presence of an acid acceptor. The acid acceptor includes, for example, alkali metal hydroxides such as sodium hydroxide or potassium hydroxide, alkaline earth metal hydroxides such as calcium hydroxide or barium hydroxide, alkali metal carbonates such as sodium carbonate or potassium carbonate, alkali metal bicarbonates such as sodium bicarbonate or potassium bicarbonate, alkali metal hydrides such as sodium hydride or potassium hydride, alkali metal lower alkoxides such as sodium ethoxide or potassium t-butoxide, lithium diisopropylamide, sodium amide, lithium amide, alkali metal fluorides such as potassium fluoride or cesium fluoride, or an organic bases such as triethylamine or tributylamine. Lower alkanones such as acetone or methylethylketone, lower alkanols such as methanol or ethanol, tetrahydrofuran, dioxane, dimethylformamide, dimethylsulfoxide or a mixture of water and the aforementioned organic solvent is preferably used as the solvent. It is preferred to carry out the reaction at a temperature of 0 to 100° C., especially 20° to 80° C.

The oxidation of the compound (IV) can be carried out by treatment with an oxidizing agent in a solvent. Methylene chloride, chloroform, lower alkanones such as acetone or methylethylketone, benzene, toluene, hexane, petroleum ether, acetonitrile, dimethylformamide, dimethylsulfoxide, acetic acid, tetrahydrofuran, dioxane or a mixture of water and the aforementioned organic solvent is preferably used as the solvent. Suitable examples of the oxidizing agent include manganese dioxide, chromic acid anhydride, potassium permanganate, acetic anhydride-dimethylsulfoxide, chloranil, 2,3-dichloro-5,6-dicyanobenzoquinone, dinitrogen tetraoxide. It is preferred to carry out the reaction at a temperature of −78° to 100° C., especially 0° to 50° C.

The reaction of the ketone compound (I-A) with the ylide compound (V) can be carried out in a solvent. Tetrahydrofuran, dimethylsulfoxide, dioxane, ether, sulfolane or a mixture thereof is preferably used as the solvent. It is preferred to carry out the reaction at a temperature of 0° to 60° C., especially 20° to 40° C.

The hydrolysis of the phenoxyacetic compound (I-C) can be carried out by treating said compound with an acid or a base in a solvent. Examples of the acid include mineral acids such as hydrochloric acid, hydrobromic acid or sulfuric acid, and examples of the base include alkali metal hydroxides such as sodium hydroxide or potassium hydroxide, alkaline earth metal hydroxides such as barium hydroxide. Lower alkanols such as methanol or ethanol, tetrahydrofuran, dioxane, dimethylformamide, dimehylsulfoxide or a mixture thereof is preferably used as the solvent. It is preferred to carry out the reaction at a temperature of 0° to 80° C., especially at 0° to 50° C. in case the acid is used, or at 20° to 60° C. in case the based is used.

When A is the 5-pyrazolyl group having either one of a lower alkoxy-lower alkyl group, a lower alkanoyl group, an arylcarbonyl group, a lower alkoxycarbonyl group or a di- or triphenyl lower alkyl group at the $N^1$-position thereof, optional removal of said substituent can be carried out in a conventional manner such as, for example, acid treatment, base treatment, hydrolysis or reduction.

Further, when A in the compound obtained in the abovementioned reactions is the 4-unsubstituted-5-pyrazolyl group, optional halogenation can be carried out by reacting said compound with a halogenating agent in a solvent. Examples of the halogenating agent include chlorine, bromine, iodine, sulfuryl halide such as sulfuryl chloride, phosphorus pentachloride, N-halogenosuccinimide such as N-chlorosuccinimide or N-bromo-succinimide, alkali metal bromite such as sodium bromite or alkali metal hypochlorite such as sodium hypochlorite. Acetic acid, dimethylformamide, methylene chloride, chloroform, dichloroethane, water or a mixture thereof is suitable as the solvent. It is preferred to carry out the reaction at a temperature of $-20°$ to $100°$ C., especially $0°$ to $60°$ C.

The thus-obtained compound (I) of the present invention can be converted into a salt thereof in a traditional manner, for example, by reacting said compound with a substantially equimolar amount of an acid or a base in a solvent.

As mentioned hereinbefore, the phenoxyacetic acid derivatives (I) of the present invention and salts thereof show potent diuretic, saluretic and uricosuric activities, and are useful for treatment and/or prophylaxis of congestive heart failure, a wide variety of edema (e.g., hepatic edema, renal edema, cardiac edema, hydrops gravidarum (=edema of pregnancy), lymphatic edema, drug-induced edema, pulmonary edema), hydrops abdominis, exudative pleurisy, interstitial nephritis, gout or hyperuremia.

The compound (I) of the present invention can be used for pharmaceutical use either in the free form or in the form of a salt thereof. Examples of the salt of the compound (I) include alkali metal salts such as sodium salt or potassium salt, alkaline earth metal salts such as calcium salt, inorganic acid addition salts such as hydrochloride or hydrobromide, organic acid addition salts such as methanesulfonate or oxalate, and the like.

The compound (I) or a salt thereof can be administered either orally or parenterally. For oral administration, the compound (I) or a salt thereof may be used in the solid form such as tablets, powders, capsules or granules, which may contain conventional carriers, binders, diluents, disintegrators, wetting agents and the like. They may also be used in liquid form such as aqueous or oily suspensions, solutions, syrups or elixir. On the other hand, for parenteral administration, the compound (I) or a salt thereof may be used, for example, in the form of injections or suppositories.

The dose of the compound (I) or a salt thereof may vary over a wide range depending on the administration route, the age, body weight or conditions of patients and the kind and severity of diseases to be treated. In general, however, preferred daily dose of the compound (I) or a salt thereof is in the range of 0.3 to 200 mg/kg/day, especially 1 to 100 mg/kg/day.

Concomitantly, the starting compound (II) in which Z is oxygen atom (said compound is hereinafter referred as the compound (II-A) may be prepared by treating a compound of the formula:

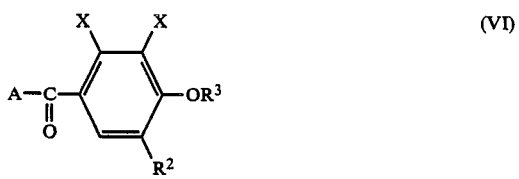

wherein $R^3$ is a lower alkyl group, and A, $R^2$ and X are the same as defined above, with hydrobromic acid, an alkali metal cyanide, an alkali metal thioacetate, boron tribromide and the like, or by oxidizing a compound of the formula:

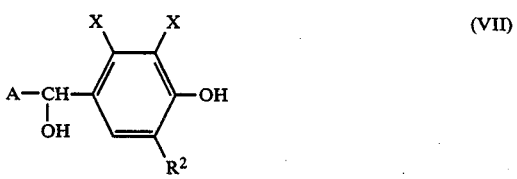

wherein A, $R^2$ and X are the same as defined above.

The starting compound (II) in which Z is methylene group may be prepared by reacting the thus-obtained compound (II-A) with the ylide compound (V).

Further, the starting compound (II) in which $R^2$ is a lower alkenyl group may also be prepared by reacting a compound of the formula:

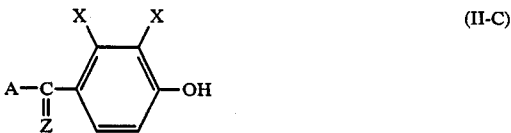

wherein A, X and Z are the same as defined above, with a lower alkenyl halide, and then subjecting the product to heating.

On the other hand, the starting compound (IV) of the present invention may be prepared by reacting the compound (VII) with the acetic acid compound (III).

Throughout the specification and claims, the terms "lower alkyl", "lower alkoxy" and "lower alkenyl" should be interpreted as referring to alkyl of one to 6 carbon atoms, alkoxy of one to 6 carbon atoms and alkenyl of 2 to 6 carbon atoms, respectively.

EXAMPLE 1

1.67 g of 2,3-dichloro-4-(1-ethoxymethyl-5-pyrazolylcarbonyl)phenol, 1.15 g of ethyl bromoacetate and 1.68 g of potassium carbonate are added to 60 ml of acetone, and the mixture is refluxed for 1 hour. The reaction mixture is filtered and the filtrate is evaporated to remove solvent. The residue is dissolved in benzene, and the solution is treated with activated charcoal and evaporated to give an oil, which is then crystallized from isopropyl ether to give 1.89 g of ethyl [2,3-dichloro-4-(1-ethoxymethyl-5-pyrazolylcarbonyl)phenoxy]acetate.

M.p. 92°–94° C.

Mass(m/e): 400 (M+).

NMR(CDCl$_3$)δ: 1.14 (t, 3H, J=7 Hz), 1.27 (t, 3H, J=7 Hz), 3.65 (q, 2H, J=7 Hz), 4.32 (q, 2H, J=7 Hz), 4.80 (s, 2H), 5.92 (s, 2H), 6.45 (d, 1H, J=2 Hz), 6.79 (d, 1H, J=9 Hz), 7.33 (d, 1H, J=9 Hz), 7.54 (d, 1H, J=2 Hz).

EXAMPLE 2

0.63 g of 2,3-dichloro-4-(1-ethoxymethyl-5-pyrazolylcarbonyl)phenol, 0.58 g of bromoacetic acid and 1.11 g of potassium carbonate are added to 40 ml of acetone, and the mixture is refluxed for 48 hours. The reaction mixture is concentrated to remove solvent, and water is added to the residue. The aqueous mixture is washed with ethyl acetate, acidified with 10% hydrochloric acid and then extracted with ethyl acetate. The extract is washed with a saturated sodium chloride solution, dried and evaporated to remove solvent. The residue is crystallized with water, and the crystals are separated by filtration, washed successively with water and isopropyl ether, and dried to give 0.42 g of [2,3-dichloro-4-(1-ethoxymethyl-5-pyrazolylcarbonyl)phenoxy]acetic acid.

M.p. 148°–149° C.

Mass(m/e): 372 (M+).

NMR(CDCl$_3$+DMSO-d$_6$)$\delta$: 1.17 (t, 3H, J=7 Hz), 3.61 (q, 2H, J=7 Hz), 4.76 (s, 2H), 5.90 (s, 2H), 6.47 (d, 1H, J=2 Hz), 6.84 (d, 1H, J=9 Hz), 7.32 (d, 1H, J=9 Hz), 7.53 (d, 1H, J=2 Hz).

Sodium salt monohydrate: M.p. 194°–196.5° C.

EXAMPLE 3 TO 12

The corresponding phenol derivatives and ethyl bromoacetate are treated in the same manner as descrived in Example 1 to give the compounds as shown in Table 1.

In Example 9 and 11, ethanol is used as the crystallization solvent instead of isopropyl ether in Example 1.

TABLE 1

| Ex. Nos. | Compound(I-a) R | Properties |
|---|---|---|
| 3 | CH$_2$OCH$_3$ | M.p. 78–79° C. Mass(m/e): 386(M+) |
| 4 | CH$_2$O(CH$_2$)$_2$OCH$_3$ | M.p. 60.5–61.5° C. Mass(m/e): 430(M+) |
| 5 | (CH$_2$)$_2$N(CH$_3$)$_2$ | oil IR$\nu_{max}^{liquid}$(cm$^{-1}$): 1750, 1660, 1580, 1555, 1505 Mass(m/e): 413(M+) |
| 6 | CH(CH$_3$)$_2$ | M.p. 79–80° C. Mass(m/e): 384(M+) |
| 7 | (CH$_2$)$_5$CH$_3$ | oil IR$\nu_{max}^{liquid}$(cm$^{-1}$): 1755, 1660, 1580, 1550, 1500 Mass(m/e): 426(M+) |
| 8 | cyclohexyl | oil IR$\nu_{max}^{liquid}$(cm$^{-1}$): 1750, 1660, 1590, 1505, Mass(m/e): 424(M+) |
| 9 | CH$_3$ | M.p. 79–80° C. Mass(m/e): 356(M+) |
| 10 | C$_2$H$_5$ | M.p. 79–81° C. Mass(m/e): 370(M+) |
| 11 | –CH$_2$–phenyl | M.p. 78–82° C. Mass(m/e): 432(M+) |
| 12 | 2,6-dimethylphenyl | oil IR$\nu_{max}^{liquid}$(cm$^{-1}$): 1755, 1670, 1580, 1550, 1495 Mass(m/e): 418(M+) |

EXAMPLE 13

1.13 g of 6-allyl-2,3-dichloro-4-(1-methyl-5-pyrazolylcarbonyl)phenol and 0.67 g of ethyl bromoacetate are treated in the same manner as described in Example 1 to give 1.44 g of ethyl [6-allyl-2,3-dichloro-4-(1-methyl-5-pyrazolylcarbonyl)phenoxy]acetate. IR$\nu_{max}^{liquid}$ (cm$^{-1}$): 1755, 1735, 1665, 1640, 1585, 1550.

Mass(m/e): 396 (M+).

EXAMPLE 14

(1) 634 mg of α-(1-ethoxymethyl-5-pyrazolyl)-2,3-dichloro-4-hydroxybenzylalcohol and 367 mg of ethyl bromoacetate are treated in the same manner as described in Example 1 to give 790 mg of α-(1-ethoxymethyl-5-pyrazolyl)-2,3-dichloro-4-ethoxycarbonylmethoxybenzylalcohol.

IR$\nu_{max}^{liquid}$ (cm$^{-1}$): 3300–3200, 1750, 1590.

Mass (m/e): 402 (M+).

(2) 770 mg of α-(1-ethoxymethyl-5-pyrazolyl)-2,3-dichloro-4-ethoxycarbonylmethoxybenzylalcohol and 1.66 g of manganese dioxide are suspended in 30 ml of methylene chloride, and the suspension is stirred at room temperature for 24 hours. The reaction mixture is filtered and the filtrate is evaporated to remove solvent. The residue is triturated with a mixture of isopropyl ether and hexane to give 703 mg of ethyl [2,3-dichloro-4-(1-ethoxymethyl-5-pyrazolylcarbonyl)phenoxy]acetate as crystals.

The physico-chemical properties of the thus-obtained product are identical with those of the compound obtained in Example 1.

EXAMPLE 15 TO 17

The corresponding phenol derivative and ethyl bromoacetate are treated in the same manner as described in Example 1 to give the compounds as shown in Table 2.

In Example 15, a mixture of isopropyl ether and hexane is used as the crystallization solvent instead of isopropyl ether in Example 1.

TABLE 2

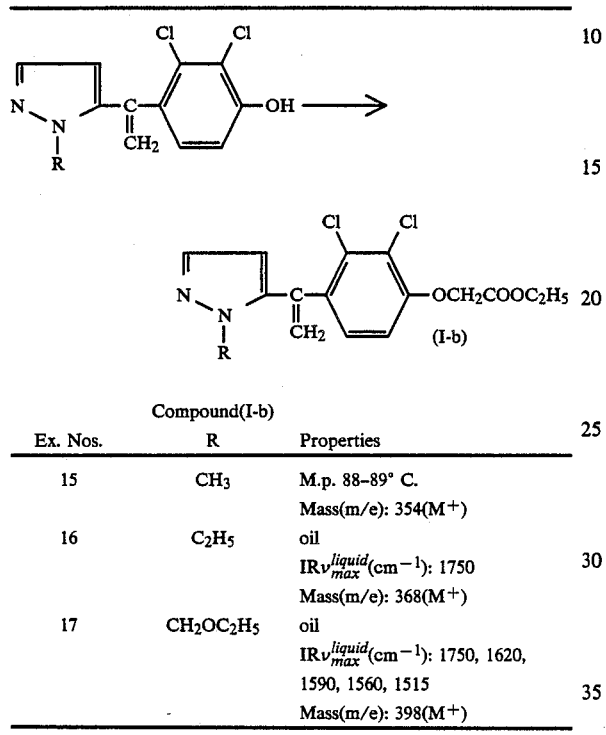

| Ex. Nos. | Compound(I-b) R | Properties |
|---|---|---|
| 15 | $CH_3$ | M.p. 88–89° C. |
|  |  | Mass(m/e): 354($M^+$) |
| 16 | $C_2H_5$ | oil |
|  |  | IR$\nu_{max}^{liquid}$(cm$^{-1}$): 1750 |
|  |  | Mass(m/e): 368($M^+$) |
| 17 | $CH_2OC_2H_5$ | oil |
|  |  | IR$\nu_{max}^{liquid}$(cm$^{-1}$): 1750, 1620, 1590, 1560, 1515 |
|  |  | Mass(m/e): 398($M^+$) |

EXAMPLE 18

0.9 g of ethyl [2,3-dichloro-4-(1-ethoxymethyl-5-pyrazolylcarbonyl)phenoxy]acetate is suspended in 20 ml of ethanol, and 10 ml of an aqueous 10% sodium hydroxide solution are added thereto. The mixture is stirred at room temperature for 1 hour. The reaction mixture is concentrated to remove ethanol and adjusted to pH 1–2 with 10% hydrochloric acid. The resulting crystals are collected by filtration, washed successively with water and isopropyl ether, and dried to give 0.82 g of [2,3-dichloro-4-(1-ethoxymethyl-5-pyrazolylcarbonyl)phenoxy]acetic acid.

The physico-chemical properties of the thus-obtained product are identical with those of the compound obtained in Example 2.

EXAMPLE 19 TO 29

The corresponding phenoxyacetate derivatives are treated in the same manner as described in Example 18 to give the compounds as shown in Table 3.

Isopropyl ether-hexane (Example 23), ethyl acetate (Example 25 and 27) or isopropyl ether (Example 24 and 28) is used as the crystallization solvent.

TABLE 3

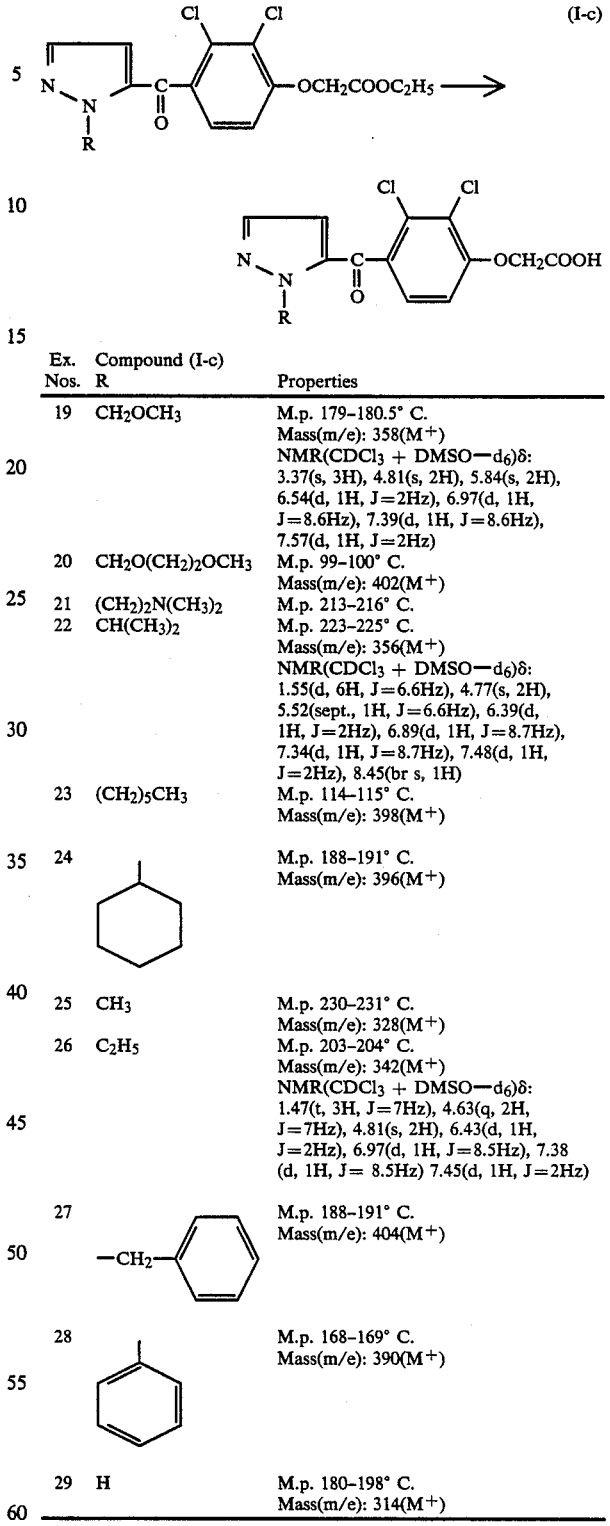

| Ex. Nos. | Compound (I-c) R | Properties |
|---|---|---|
| 19 | $CH_2OCH_3$ | M.p. 179–180.5° C. |
|  |  | Mass(m/e): 358($M^+$) |
|  |  | NMR(CDCl$_3$ + DMSO—d$_6$)δ: 3.37(s, 3H), 4.81(s, 2H), 5.84(s, 2H), 6.54(d, 1H, J=2Hz), 6.97(d, 1H, J=8.6Hz), 7.39(d, 1H, J=8.6Hz), 7.57(d, 1H, J=2Hz) |
| 20 | $CH_2O(CH_2)_2OCH_3$ | M.p. 99–100° C. |
|  |  | Mass(m/e): 402($M^+$) |
| 21 | $(CH_2)_2N(CH_3)_2$ | M.p. 213–216° C. |
| 22 | $CH(CH_3)_2$ | M.p. 223–225° C. |
|  |  | Mass(m/e): 356($M^+$) |
|  |  | NMR(CDCl$_3$ + DMSO—d$_6$)δ: 1.55(d, 6H, J=6.6Hz), 4.77(s, 2H), 5.52(sept., 1H, J=6.6Hz), 6.39(d, 1H, J=2Hz), 6.89(d, 1H, J=8.7Hz), 7.34(d, 1H, J=8.7Hz), 7.48(d, 1H, J=2Hz), 8.45(br s, 1H) |
| 23 | $(CH_2)_5CH_3$ | M.p. 114–115° C. |
|  |  | Mass(m/e): 398($M^+$) |
| 24 | cyclohexyl | M.p. 188–191° C. |
|  |  | Mass(m/e): 396($M^+$) |
| 25 | $CH_3$ | M.p. 230–231° C. |
|  |  | Mass(m/e): 328($M^+$) |
| 26 | $C_2H_5$ | M.p. 203–204° C. |
|  |  | Mass(m/e): 342($M^+$) |
|  |  | NMR(CDCl$_3$ + DMSO—d$_6$)δ: 1.47(t, 3H, J=7Hz), 4.63(q, 2H, J=7Hz), 4.81(s, 2H), 6.43(d, 1H, J=2Hz), 6.97(d, 1H, J=8.5Hz), 7.38 (d, 1H, J= 8.5Hz) 7.45(d, 1H, J=2Hz) |
| 27 | —CH$_2$—phenyl | M.p. 188–191° C. |
|  |  | Mass(m/e): 404($M^+$) |
| 28 | phenyl | M.p. 168–169° C. |
|  |  | Mass(m/e): 390($M^+$) |
| 29 | H | M.p. 180–198° C. |
|  |  | Mass(m/e): 314($M^+$) |

EXAMPLE 30

1.44 g of ethyl [6-allyl-2,3-dichloro-4-(1-methyl-5-pyrazolylcarbonyl)phenoxy]acetate are treated in the same manner as described in Example 18 except that a mixture of ether and hexane is used as the crystallization solvent. 1.19 g of [6-allyl-2,3-dichloro-4-(1-methyl-5- pyrazolylcarbonyl)phenoxy]acetic acid are obtained as crystals.

M.p. 111°–113° C.
Mass (m/e): 368 (M+).
NMR(CDCl$_3$)δ: 3.54 (m, 2H), 4.30 (s, 3H), 4.72 (s, 2H), 4.9–5.3 (m, 2H), 5.4–6.1 (m, 1H), 6.42 (d, 1H, J=2 Hz), 7.21 (s, 1H), 7.49 (d, 1H, J=2 Hz), 9.29 (broad s, 1H).

EXAMPLE 31 TO 34

The corresponding phenoxyacetate derivatives are treated in the same manner as described in Example 18 to give the compounds as shown in Table 4.

In Example 34, ethanol-isopropyl ether is used as the crystallization solvent.

TABLE 4

(I-d)

[Structure: pyrazole-N-R connected via C(=CH$_2$) to 2,3-dichlorophenyl bearing OCH$_2$COOC$_2$H$_5$] →

[Structure: pyrazole-N-R connected via C(=CH$_2$) to 2,3-dichlorophenyl bearing OCH$_2$COOH]

| Ex. Nos. | Compound (I-d) R | Properties |
|---|---|---|
| 31 | H | M.p. 205–207° C. Mass(m/e): 312(M+) |
| 32 | CH$_3$ | M.p. 186.5–187.5° C. Mass(m/e): 326(M+) NMR(CDCl$_3$ + DMSO—d$_6$)δ: 3.75(s, 3H), 4.71(s, 2H), 5.53(s-like, 1H), 5.61(s-like, 1H), 6.03(d, 1H, J=2 Hz), 6.79(d, 1H, J=8.5Hz), 7.16(d, 1H, J=8.5Hz), 7.38(d, 1H, J=2Hz) |
| 33 | CH$_2$OC$_2$H$_5$ | M.p. 151.5–153.5° C. Mass(m/e): 370(M+) NMR(CDCl$_3$ + DMSO—d$_6$)δ: 1.16(t, 3H, J=7Hz), 3.63(q, 2H, J=7Hz), 4.72(s, 2H), 5.43(s, 2H), 5.53(s-like, 1H), 5.97(s-like, 1H), 6.83(d, 1H, J=8.5Hz), 7.25(d, 1H, J=8.5Hz), 7.42(d-like, 2H) |
| 34 | C$_2$H$_5$ | M.p. 163.5–153.5° C. Mass(m/e): 340(M+) |

EXAMPLE 25

1.03 g of ethyl [2,3-dichloro-4-(1-ethoxymethyl-5-pyrazolylcarbonyl)phenoxy]acetate are dissolved in 25 ml of ethanol, and 6 ml of concentrated hydrochloric acid are added thereto. The mixture is stirred at 60°–65° C. for 3.5 hours. The reaction mixture is cooled, adjusted to pH 8–9 by addition of an aqueous saturated sodium bicarbonate solution under ice-cooling, and then extracted with ethyl acetate. The extract is washed successively with an aqueous saturated sodium bicarbonate solution and water, dried and evaporated to remove solvent. The residue is purified by silica gel column chromatography (solvent; benzene-ethyl acetate) and crystallized with a mixture of benzene and chloroform to give 0.54 g of ethyl [2,3-dichloro-4-(5-pyrazolylcarbonyl)phenoxy]acetate.

M.p. 147°–149° C.
Mass (m/e): 342 (M+).

EXAMPLE 36

1.10 g of ethyl {2,3-dichloro-4-[1-(1-ethoxymethyl-5-pyrazolyl)vinyl]phenoxy}acetate are treated in the same manner as described in Example 35 except that isopropyl ether is used as the crystallization solvent. 0.81 g of ethyl {2,3-dichloro-4-[1-(5-pyrazolyl)vinyl]phenoxy}acetate is obtained as crystals.

M.p. 110°–112° C.
Mass (m/e): 340 (M+).
NMR(CDCl$_3$)δ: 1.31 (t, 3H, J=7 Hz), 4.31 (q, 2H, J=7 Hz), 4.75 (s, 2H), 5.24 (s, 1H), 5.97 (s, 1H), 6.19 (d, 1H, J=2 Hz), 6.81 (d, 1H, J=8.8 Hz), 7.23 (d, 1H, J=8.5 Hz), 7.4 (broad s, 1H), 7.48 (d, 1H, J=2 Hz).

EXAMPLE 37

6.7 g of an aqueous 10% sodium hypochlorite solution are added dropwise to a solution of 2.36 g of [2,3-dichloro-4-(1-ethyl-5-pyrazolylcarbonyl)phenoxy]acetic acid in a mixture of 50 ml of acetic acid and 20 ml of dimethylformamide, and the mixture is stirred at room temperature for 30 minutes. A solution of 2.0 g of sodium thiosulfate in 5 ml of water is added to the reaction mixture to decompose excess sodium hypochloride, and the mixture is evaporated to remove solvent. The residue (oil) is dissolved in water, and the solution is adjusted to pH 3 with 1N hydrochloric acid and extracted with ethyl acetate. The extract is washed with water, dried and evaporated to remove solvent. The residue is crystallized from a mixture of ethyl acetate and hexane to give 2.19 g of [2,3-dichloro-4-(4-chloro-1-ethyl-5-pyrazolylcarbonyl)phenoxy]acetic acid.

M.p. 156°–160° C.
Mass (m/e): 376 (M+).
NMR(DMSO-d$_6$)δ: 1.39 (t, 3H, J=7 Hz), 4.45 (q, 2H, J=7 Hz), 4.97 (s, 2H), 7.23 (d, 1H, J=8 Hz), 7.54 (d, 1H, J=8.8 Hz), 7.74 (s, 1H).

EXAMPLE 38

A solution of 1.88 g of sodium bromite trihydrate in 5 ml of water is added dropwise at room temperature to a solution of 1.85 g of ethyl [2,3-dichloro-4-(1-ethyl-5-pyrazolylcarbonyl)phenoxy]acetate and the mixture is stirred at room temperature for 15 hours. The reaction mixture is evaporated to remove solvent and the residue is dissolved in 20 ml of water. The aqueous solution is made alkaline with a saturated sodium bicarbonate solution and extracted with ethyl acetate. The extract is washed with water, dried and evaporated to remove solvent. The residue is crystallized with a mixture of isopropyl ether and hexane to give 1.98 g of ethyl [2,3-dichloro-4-(4-bromo-1-ethyl-5-pyrazolylcarbonyl)phenoxy]acetate.

M.p. 90°–91° C.
Mass (m/e): 450 (M+).
NMR(CDCl$_3$)δ: 1.30 (t, 3H, J=7.3 Hz), 1.48 (t, 3H, J=3 Hz), 4.28 (q, 2H, J=7.3 Hz), 4.54 (q, 2H, J=7.3 Hz), 4.78 (s, 2H), 6.84 (d, 1H, J=8.6 Hz), 7.32 (d, 1H, J=8.6 Hz), 7.47 (s, 1H).

EXAMPLE 39

5 ml of an aqueous 4.3N sodium hydroxide solution is added dropwise under ice-cooling to a solution of 1.92 g of ethyl [2,3-dichloro-4-(4-bromo-1-ethyl-5-pyrazolylcarbonyl)phenoxy]acetate in 20 ml of methanol and the mixture is stirred at room temperature for 20 minutes. The reaction mixture is adjusted to pH 1–2 with 1N hydrochloric acid, and 20 ml of water is added thereto.

The mixture is extracted with ethyl acetate, and the extract ia washed with water, dried and evaporated to remove solvent. The residue is crystallized with a mixture of ethyl acetate and hexane to give 1.72 g of [2,3-dichloro-4-(4-bromo-1-ethyl-5-pyraolylcarbonyl)-phenoxy]acetic acid.

M.p. 169°–172° C.

Mass (m/e): 432 (M+).

NMR(DMSO-d$_6$)δ: 1.38 (t, 3H, J=6.8 Hz), 4.44 (q, 2H, J=2.8 Hz), 4.98 (s, 2H), 7.25 (d, 1H, J=8.8 Hz), 7.54 (d, 1H, J=8.8 Hz), 7.76 (s, 1H).

[PREPARATION OF STARTING COMPOUNDS]

Preparation 1

(1) 4.13 ml of 1.6M n-butyl lithium in hexane are added dropwise to a tetrahydrfuran solution of 0.76 g of 1-ethoxymethylpyrazole at −60° C. under argon gas atmosphere. the mixture is stirred at −63° to −50° C. for 1 hour. A solution of 1.23 g of 2,3-dichloro-4-methoxybenzaldehyde in tetrahydrofuran is added to the mixture, and the mixture is stirred at −50° C. to room temperature for 1 hour. An aqueous saturated ammonium chloride solution and water are added to the mixture under ice-cooling and the mixture is concentrated to remove tetrahydrofuran. The residual aqueous layer is extracted with ethyl acetate and the extract is washed with water, dried and evaporated to give colorless crystals, which are then washed with isopropyl ether and dried to give 1.62 g of α-(1-ethoxymethyl-5-pyrazolyl)-2,3-dichloro-4-methoxy-benzylalcohol.

M.p. 155°–157° C.

(2) 2.72 g of manganese dioxide are added to a solution of 1.04 g of α-(1-ethoxymethyl-5-pyrazolyl)-2,3-dichloro-4-methoxybenzylalcohol in methylene chloride and the mixture is stirred at room temperature for 27 hours. The reaction mixture is filtered and the filtrate is condensed to an oily residue, which is then crystallized from isopropyl ether to give 0.93 g of (2,3-dichloro-4-methoxyphenyl)(1-ethoxymethyl-5-pyrazolyl)methanone.

M.p. 74°–76° C.

(3) 9.45 g of potassium thiolacetate are added to a solution of 5.45 g of (2,3-dichloro-4-methoxyphenyl)(1-ethoxymethyl-5-pyrazolyl)methanone in dimethylsulfoxide and the mixture is stirred at 90°–100° C. under argon gas atmosphere for 4 hours. After cooling the solution, cold water is added thereto, and the mixture is adjusted to pH 5–6 with acetic acid and then extracted with ethyl acetate. The extract is washed with water, dried and evaporated to remove solvent. The residue is purified by silica gel column chromatography to give 3.72 g of 2,3-dichloro-4-(1-ethoxymethyl-5-pyrazolyl-carbonyl)phenol.

M.p. 115°–117° C.

Preparation 2

(1) 6.0 g of 1-methylpyrazole are treated in the same manner as described in Preparation 1-(1). 18.0 g of α-(1-methyl-5-pyrazolyl)-2,3-dichloro-4-methxybenzylalcohol are obtained.

M.p. 169°–171° C.

(2) 2.23 g of α-(1-methyl-5-pyrazolyl)-2,3-dichloro-4-methxybenzylalcohol are dissolved in a mixture of acetic acid, acetone and water, and 0.90 g of chromic acid anhydride is added to the solution. The mixture is stirred at room temperature for 2.5 hours and isopropanol is added thereto to encompose excess oxidizing agent. The mixture is filtered and the filtrate is evaporated. Water is added to the residue and the mixture is extracted with chloroform. The extract is washed, dried and evaporated to remove solvent. The residue is crystallized with methanol to give 2.07 g of (2,3-dichloro-4-methoxyphenyl)(1-methyl-5-pyrazolyl)methanone.

M.p. 150°–152° C.

(3) 20 ml of 47% hydrobromic acid are added to 1.0 g of (2,3-dichloro-4-methoxyphenyl)(1-methyl-5-pyrazolyl)methanone, and the mixture is refluxed for 4 hours. The reaction mixture is evaporated to remove solvent and the residue is dissolved in an aqueous 10% sodium hydroxide solution. The solution is filtered, and the filtrate is adjusted to pH 4–5 with acetic acid. The resultant crystals are collected, washed with water and dried to give 0.88 g of 2,3-dichloro-4-(1-methyl-pyrazolylcarbonyl)phenol.

M.p. 220°–222° C.

Preparation 3

(1) 1.00 g of 1-benzylpyrazole is treated in the same manner as described in Example 1-(1) and 2-(2) to give 2.07 g of (2,3-dichloro-4-methoxyphenyl)(1-benzyl-5-pyrazolyl)methanone.

M.p. 102.5°–105° C.

(2) 0.95 g of sodium cyanide is added to a solution of 1.0 g of (2,3-dichloro-4-methoxyphenyl)(1-benzyl-5-pyrazolyl)methanone in dimethylsulfoxide and the mixture is heated at 100° C. for 4 hours under argon gas atmosphere. After cooling, cold water is added to the reaction mixture. The mixture is adjusted to pH 5–6 with acetic acid and then extracted with ethyl acetate. The extract is washed with water, dried and evaporated to remove solvent. The residue is purified by silica gel column chromatography to give 0.39 g of 2,3-dichloro-4-(1-benzyl-5-pyrazolylcarbonyl)phenol.

M.p. 131°–133° C.

Preparation 4–11

The corresponding starting compounds are treated in the same manner as described in Preparation 1, 2 or 3 to give the compounds as shown in Table 5

TABLE 5

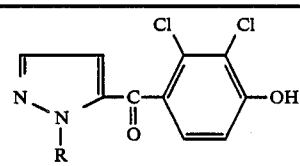

(II-a)

| Pr. Nos. | Compound (II-a) R | Melting points (°C.) |
|---|---|---|
| 4 | CH$_2$OCH$_3$ | 134–135 |
| 5 | CH$_2$O(CH$_2$)$_2$OCH$_3$ | 92–93 |
| 6 | (CH$_2$)$_2$N(CH$_3$)$_2$ | 176–177 |
| 7 | CH(CH$_3$)$_2$ | 191–192 |
| 8 | (CH$_2$)$_5$CH$_3$ | 110–111.5 |
| 9 | cyclohexyl | 161–162.5 |
| 10 | C$_2$H$_5$ | 180–181 |

TABLE 5-continued $$\text{(II-a)}$$

(structure shown: pyrazolyl-C(=O)-phenyl with Cl, Cl, OH substituents; N-R on pyrazole)

| Pr. Nos. | Compound (II-a) R | Melting points (°C.) |
|---|---|---|
| 11 | (phenyl group) | 160–161 |

Preparation 12

(1) A suspension of 8.35 g of 2,3-dichloro-4-(1-methyl-5-pyrazolylcarbonyl)phenol, 5.59 g of allyl bromide and 10.64 g of potassium carbonate in acetone is refluxed for 3 hours. The reaction mixture is filtered and the filtrate is evaporated to remove solvent. The residue is dissolved in toluene, and the solution is treated with activated charcoal and then evaporated to give 8.36 g of (2,3-dichloro-4-allyloxyphenyl)(1-methyl-5-pyrazolyl)methanone.
M.p. 118°–119° C.

(2) A suspension of 8.20 g of (2,3-dichloro-4-allyloxyphenyl)(1-methyl-5-pyrazolyl)methanone in N,N-dimethylaniline is stirred at 200° C. under argon gas atmosphere for 25 hours and cooled. The reaction mixture is diluted with ether and extracted with an aqueous 5% sodium hydroxide solution. The aqueous extract is washed with ether, adjusted to pH 5–6 with acetic acid and then extracted with chloroform. The organic layer is washed with water, dried and evaporated to give a solid, which is then purified by silica gel column chromatography to give 5.16 g of 6-allyl-2,3-dichloro-4-(1-methyl-5-pyrazolylcarbonyl)phenol.
M.p. 141°–143° C.

Preparation 13

A solution of 2.71 g of 2,3-dichloro-4-(1-methyl-5-pyrazolylcarbonyl)phenol in tetrahydrofuran-dimethylsulfoxide is added dropwise to an ylide solution prepared from a solution of 8.57 g of methyltriphenylphophonium bromide in tetrahydrofurandimethylsulfoxide and 13.8 ml of 1.6M n-butyl lithium in hexane. The mixture is stirred at room temperature for 18 hours, and further stirred at 65° C. for 2 hours. The reaction mixture is poured into an aqueous saturated ammonium chloride solution and then extracted with ethyl acetate. The extract is washed with water, dried and evaporated to remove solvent. The residue is purified by silica gel column chromatography to give 2.41 g of 2,3-dichloro-4-[1-(1-methyl-5-pyrazolyl)vinyl]phenol.
M.p. 185°–186.5° C.

Preparation 14 and 15

The corresponding ketone compounds are treated in the same manner as described in Preparation 13 to give the following compounds.

(14) 2,3-dichloro-4-[1-(1-ethyl-5-pyrazolyl)vinyl]phenol
M.p. 180°–182.5° C.

(15) 2,3-dichloro-4-[1-(1-ethoxymethyl-5-pyrazolyl)vinyl]phenol
M.p. 162°–164° C.

Preparation 16

(1) A solution of 5.51 g of boron tribromide in methylene chloride is added dropwise to a solution of 2.05 g of 2,3-dichloro-4-methoxybenzaldehyde in methylene chloride. The mixture is stirred at room temperature for 4 hours, poured into ice-water and then extracted with ethyl acetate. The extract is washed with water, dried and evaporated to remove solvent. 10% hydrochloric acid and methanol are added to the residue and the mixture is stirred for 3 hours under ice-cooling and extracted with ethyl acetate again. The extract is washed with water, dried and evaporated to remove solvent. The residue is crystallized with isopropyl ether to give 1.82 g of 4-hydroxy-2,3-dichlorobenzaldehyde.

(2) 18.1 ml of 1.6M n-butyl lithium in hexane are added to a tetrahydrofuran solution of 3.56 g of 1-ethoxymethylpyrazole at −55° to −53° C. under argon gas atmosphere and the mixture is stirred at the same temperature for 1 hour. A solution of 2.45 g of 2,3-dichloro-4-hydroxybenzaldehyde in tetrahydrofuran is added to the above mixture, and the reaction mixture is stirred at −55° to −60° C. for 3 hours. 4.9 ml of hexamethylphosphoric triamide are then added and the whole mixture is stirred at room temperature for 16 hours. An aqueous saturated ammonium chloride solution is added and the mixture is extracted with ethyl acetate. The extract is washed with water, dried and evaporated to remove solvent. The residue is purified by silica gel column chromatography and crystallized with a mixture of ethyl acetate and isopropyl ether to give 2.69 g of α-(1-ethoxymethyl-5-pyrazolyl)-2,3-dichloro-4-hydroxybenzylalcohol.
M.p. 149.5°–150° C.

What we claim is:

1. A phenoxyacetic acid derivative of the formula:

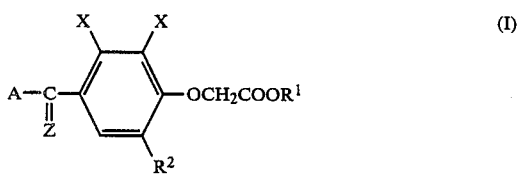

$$\text{(I)}$$

wherein A is 5-pyrazolyl group or a 5-pyrazolyl group having at least one substituent selected from a halogen atom, an alkyl ($C_{1-10}$) group, a cycloalkyl ($C_{3-8}$) group, a phenyl group, a phenyl-lower alkyl group, a lower alkoxy-lower alkyl group, a lower alkoxy-lower alkoxy-lower alkyl group, a di(lower alkyl)amino-lower alkyl group, a lower alkanoyl group, benzoyl group and a di-or triphenyl-lower alkyl group, $R^1$ is hydrogen atom or a lower alkyl group, $R^2$ is hydrogen atom or a lower alkenyl group, X is a halogen atom and Z is oxygen atom or methylene group, or a pharmaceutically acceptable salt thereof.

2. The compound according to claim 1, in which A is 5-pyrazolyl group or a 5-pyrazolyl group having an at least one substituent selected from a halogen atom, alkyl($C_{1-10}$) group, a cycloalkyl($C_{3-8}$) group, phenyl group, a phenyl-lower alkyl group, a lower alkoxy-lower alkyl group, a lower alkoxy-lower alkoxy-lower alkyl group and a di(lower alkyl) amino-lower alkyl group, $R^2$ is hydrogen atom or allyl group and X is chlorine atom.

3. The compound according to claim 2, in which $R^1$ is hydrogen atom.

4. The compound according to claim 2, in which A is 5-pyrazolyl group, a 1-lower alkyl-5-pyrazolyl group, a 1-lower alkyl-4-halogeno-5-pyrazolyl group, a 1-cycloalkyl($C_{3-8}$)-5-pyrazolyl group, 1-phenyl-5-pyrazolyl group, a 1-(phenyl-lower alkyl)-5-pyrazolyl group, a 1-(lower alkoxy-lower alkyl)-5-pyrazolyl group, a 1-(lower alkoxy-lower alkoxy-lower alkyl)-5-pyrazolyl group or a 1-(di(lower alkyl)amino-lower alkyl)-5-pyrazolyl group.

5. The compound according to claim 4, in which $R^1$ is hydrogen atom.

6. The compound according to claim 4, in which A is a 1-lower alkyl-5-pyrazolyl group, a 1-lower alkyl-4-halogeno-5-pyrazolyl group or a 1-(lower alkoxy-lower alkyl)-5-pyrazolyl, and $R^1$ is hydrogen atom.

7. The compound according to claim 6, which is [2,3-dichloro-4-(1-ethyl-5-pyrazolylcarbonyl)phenoxy]acetic acid or a pharmaceutically acceptable salt thereof.

8. The compound according to claim 6, which is {2,3-dichloro-4-[1-(1-ethoxymethyl-5-pyrazolyl)vinyl]phenoxy}acetic acid or a pharmaceutically acceptable salt thereof.

9. The compound according to claim 6, which is [2,3-dichloro-4-(4-chloro-1-ethyl-5-pyrazolylcarbonyl)phenoxy]acetic acid or a pharmaceutically acceptable salt thereof.

10. A pharmaceutical composition exhibiting diuretic and uricosuric effects which comprises a diuretically and uricosurically effective amount of the compound claimed in claim 1 and a pharmaceutically acceptable carrier therefor.

11. A method for treatment or prophylaxis of congestive heart failure, edema, hydrops abdominis, exudative pleurisy, interstitial nephritis, gout or hyperuremia in a warm-blooded animal which comprises administering to said warm-blooded animal an effective amount for said treatment or prophylaxis of the compound claimed in claim 1.

12. A method according to claim 11 wherein said effective amount comprises a dose of 0.3 to 200 mg/kg/day.

13. A method for achieving diuretic and uricosuric effects in a warm-blooded animal, which comprises administering to said warm-blooded animal a diuretically and uricosurically effective amount of the compound claimed in claim 1.

* * * * *